(12) United States Patent
Koktzoglou (10) Patent No.: US 9,968,276 B2
(45) Date of Patent: May 15, 2018

(54) SYSTEM AND METHOD FOR IMAGING OF THE VASCULAR COMPONENTS WITH TEMPORAL INFORMATION AND SUPPRESSED BLOOD POOLS USING MAGNETIC RESONANCE IMAGING

(71) Applicant: Ioannis Koktzoglou, Des Plaines, IL (US)

(72) Inventor: Ioannis Koktzoglou, Des Plaines, IL (US)

(73) Assignee: NORTHSHORE UNIVERSITY HEALTHSYSTEM, Evanston, IL (US)

( * ) Notice: Subject to any disclaimer, the term of this patent is extended or adjusted under 35 U.S.C. 154(b) by 1308 days.

(21) Appl. No.: 13/647,119

(22) Filed: Oct. 8, 2012

(65) Prior Publication Data

US 2014/0100443 A1 Apr. 10, 2014

(51) Int. Cl.
*A61B 5/055* (2006.01)
*G01R 33/563* (2006.01)
(Continued)

(52) U.S. Cl.
CPC ............ *A61B 5/055* (2013.01); *A61B 5/0044* (2013.01); *A61B 5/0263* (2013.01);
(Continued)

(58) Field of Classification Search
CPC ............ G01R 33/5635; G01R 33/4838; G01R 33/4828; G01R 33/5607; G01R 33/56325;
(Continued)

(56) References Cited

U.S. PATENT DOCUMENTS

| 7,941,204 B1* | 5/2011 | Wang ................. | G01R 33/4824 324/307 |
| 2008/0161678 A1* | 7/2008 | Miyazaki ............. | A61B 5/0263 600/419 |

(Continued)

OTHER PUBLICATIONS

Koktzoglou, Ioannis, et al. "Dark-blood MRI of the thoracic aorta with 3D diffusion-prepared steady-state free precession: initial clinical evaluation." American Journal of Roentgenology 189.4 (2007): 966-972.*

(Continued)

*Primary Examiner* — Rishi Patel
(74) *Attorney, Agent, or Firm* — Quarles & Brady LLP (57) ABSTRACT

A system and method is provided that includes a) monitoring a cardiac cycle of the subject to identify a predetermined point and, b) upon identifying the predetermined point, performing the steps of i) performing at least one of a desired number of magnetization suppressing preparations to suppress signal from blood flow through at least the region of interest, ii) acquiring a first set of imaging data from the region of interest, and iii) repeating step i) and step ii) to acquire at least a second set of imaging data from the region of interest. The method further includes c) repeating step b) a predetermined number of times over a series of cardiac cycles to acquire respective sets of medical imaging data of the region of interest and d) reconstructing first set of imaging data and the second set of imaging data into a time-resolved series of images.

18 Claims, 8 Drawing Sheets

(51) Int. Cl.
- G01R 33/56 (2006.01)
- A61B 5/00 (2006.01)
- A61B 5/026 (2006.01)
- A61B 5/0452 (2006.01)

(52) U.S. Cl.
CPC .......... *A61B 5/7285* (2013.01); *G01R 33/563* (2013.01); *G01R 33/5607* (2013.01); *G01R 33/5635* (2013.01); *A61B 5/0452* (2013.01)

(58) Field of Classification Search
CPC ....... G01R 33/563; A61B 5/055; A61B 5/004; A61B 5/0044; A61B 5/0263; A61B 5/0452; A61B 5/7285
See application file for complete search history.

(56) References Cited

U.S. PATENT DOCUMENTS

| | | | | |
|---|---|---|---|---|
| 2010/0134103 | A1* | 6/2010 | Edelman | G01R 33/5635 324/309 |
| 2012/0262175 | A1* | 10/2012 | Alsop | G01R 33/5607 324/314 |
| 2013/0257429 | A1* | 10/2013 | Edelman | G01R 33/5635 324/309 |

OTHER PUBLICATIONS

Balu, et al., Carotid Plaque Assessment Using Fast 3D Isotropic-Resolution Black-Blood MRI, Magnetic Resonance in Medicine, 2011, 65(3):627-637.

Barger, et al., Time-Resolved Contrast-Enhanced Imaging with Isotropic Resolution and Broad Coverage Using an Undersampled 3D Projection Trajectory, Magnetic Resonance in Medicine, 2002, 48(2):297-305.

Bornstedt, et al., Local Excitation Black Blood Imaging at 3T: Application to the Carotid Artery Wall, Magnetic Resonance in Medicine, 2008, 59(5):1207-1211.

Edelman, et al., Extracranial Carotid Arteries: Evaluation with "Black Blood" MR Angiography, Radiology, 1990, 177:45-50.

Edelman, et al., Fast Selective Black Blood MR Imaging, Radiology, 1991, 181:655-660.

Fahmy, et al., Artifact-Free Black-Blood Cine Cardiac Imaging in a Single Breath-Hold, Magnetic Resonance Imaging, 2006, 24(10):1303-1310.

Fischer, et al., Limitations of Stimulated Echo Acquisition Mode (STEAM) Techniques in Cardiac Applications, Magnetic Resonance in Medicine, 1995, 34(1):80-91.

Frahm, et al., High-Speed STEAM MRI of the Human Heart, Magnetic Resonance in Medicine, 1991, 22(1):133-142.

Ibrahim, et al., Stimulated-Echo Acquisition Mode (STEAM) MRI for Black-Blood Delayed Hyperenhanced Myocardial Imaging, Journal of Magnetic Resonance Imaging, 2008, 27:229-238.

Koktzoglou, et al., Diffusion-Prepared Segmented Steady-State Free Precession: Application to 3D Black-Blood Cardiovascular Magnetic Resonance of the Thoracic Aorta and Carotid Artery Walls, Journal of Cardiovascular Magnetic Resonance, 2007, 9(1):33-42.

Mendes, et al., CINE Turbo Spin Echo Imaging, Magnetic Resonance in Medicine, 2011, 66(5):1286-1292.

Song, et al., k-Space Weighted Image Contrast (KWIC) for Contrast Manipulation in Projection Reconstruction MRI, Magnetic Resonance in Medicine, 2000, 44(6):825-832.

* cited by examiner

SYSTEM AND METHOD FOR IMAGING OF THE VASCULAR COMPONENTS WITH TEMPORAL INFORMATION AND SUPPRESSED BLOOD POOLS USING MAGNETIC RESONANCE IMAGING

CROSS-REFERENCE TO RELATED APPLICATIONS

N/A

FIELD OF THE INVENTION

The invention relates to a system and method for performing magnetic resonance imaging and, more particularly, to a system and method for acquiring images using magnetic resonance imaging that allow clinical review of a subject's vascular components, including the blood vessels and the heart, over time and without signal from blood pools within the vessels or heart obscuring the vascular components.

BACKGROUND OF THE INVENTION

When a substance such as human tissue is subjected to a uniform magnetic field (polarizing field $B_0$), the individual magnetic moments of the nuclear spins in the tissue attempt to align with this polarizing field, but precess about it in random order at their characteristic Larmor frequency. Usually the nuclear spins are comprised of hydrogen atoms, but other NMR active nuclei are occasionally used. A net magnetic moment $M_z$ is produced in the direction of the polarizing field, but the randomly oriented magnetic components in the perpendicular, or transverse, plane (x-y plane) cancel one another. If, however, the substance, or tissue, is subjected to a magnetic field (excitation field $B_1$; also referred to as the radiofrequency (RF) field) which is in the x-y plane and which is near the Larmor frequency, the net aligned moment, $M_z$, may be rotated, or "tipped" into the x-y plane to produce a net transverse magnetic moment $M_t$, which is rotating, or spinning, in the x-y plane at the Larmor frequency. The practical value of this phenomenon resides in the signal which is emitted by the excited spins after the excitation field $B_1$ is terminated. There are a wide variety of measurement sequences in which this nuclear magnetic resonance ("NMR") phenomenon is exploited.

When utilizing these signals to produce images, magnetic field gradients ($G_x$, $G_y$, and $G_z$) are employed. Typically, the region to be imaged experiences a sequence of measurement cycles in which these gradients vary according to the particular localization method being used. The emitted MR signals are detected using a receiver coil. The MRI signals are then digitized and processed to reconstruct the image using one of many well-known reconstruction techniques.

Carotid artery atherosclerosis is a main cause of stroke and a major source of mortality and morbidity. Despite the relatively high prevalence of atherosclerosis at the carotid bifurcation, it remains difficult to predict which patients will experience devastating stroke. In the quest to identify carotid atherosclerotic lesions at risk for producing stroke, magnetic resonance imaging has found increasing utilization due to its non-invasive nature, excellent soft-tissue contrast, and ability to characterize carotid plaque structure and composition.

Numerous MRI protocols have been designed to image the structure and composition of the carotid arterial wall. A property of many of these protocols is the suppression of the arterial blood pool, which provides for clear delineation of the arterial wall from the lumen. Suppression of the blood pool is accomplished through application of specialized magnetization preparations including regional saturation bands, inversion-recovery based methods, and motion spoiling gradients. These magnetization preparations, however, each suffer from limitations that reduce the clinical utility. For example, some use quiescent inversion delay times to suppress the blood pool, are best suited for thin and non-contiguous section imaging, or suppress the blood pool for only a brief period of time.

Given these constraints and the general requirement of high spatial resolution imaging to adequately define the arterial wall, reported dark blood arterial wall MR protocols have largely been limited to static imaging protocols that, by definition and design, lack temporal resolution. These static imaging protocols, which may be in either two or three spatial dimensions, do not have the ability to display vascular pulsation occurring over the cardiac cycle, which limits the clinical usefulness of the information collected in the imaging process.

Recently, it was reported in Mendes J, Parker D L, Hulet J, Treiman G S, Kim S E. CINE turbo spin echo imaging. Magn Reson Med 2011; 66(5):1286-1292 that cardiac phase-resolved dark blood display of the carotid arteries could be achieved using a multi-slice 2D fast spin-echo protocol. However, this imaging technique provides only a limited extent of vascular coverage, cannot provide contiguous data with fine isotropic spatial resolution, and has not been validated against other measures of arterial distension.

Clinicians believe that the ability to precisely visualize and quantify motion carotid atherosclerosis throughout the cardiac cycle may enable better characterization of the disease and prognosticate future cerebrovascular events. Unfortunately, there is no MRI method that provides large coverage dark-blood display of the carotid arteries with submillimeter isotropic spatial resolution over the cardiac cycle.

Therefore, it would be desirable to have a system and method for acquiring a plurality of 3D, time-resolved image sets over the cardiac cycle in a clinical reasonable scan time and without signal from blood within the vascular or cardiac structures obscuring clinically useful information.

SUMMARY OF THE INVENTION

The present invention overcomes the aforementioned drawbacks by providing a magnetic resonance imaging technique for acquiring four-dimensional (4D), dark blood images of vascular or cardiac structures. The technique can be applied to image the human vascular system including the carotid arteries. The technique can be readily validated against established cineangiographic bright-blood and static dark-blood MR techniques to facilitate faster clinical adoption.

In accordance with one aspect of the invention, a method for acquiring medical images of a portion of a vascular structure of a subject using a magnetic resonance imaging (MRI) system is disclosed. The method includes a) determining a desired number of magnetization suppressing preparations to be applied to the subject within one cardiac cycle of the subject to sustain a suppression of signal from blood flow through at least a region of interest. The method also includes b) monitoring a cardiac cycle of the subject to identify a predetermined point in the cardiac cycle. Upon identifying the predetermined point in the cardiac cycle, the method includes i) performing at least one of the desired number of magnetization suppressing preparations to suppress signal from blood flow through at least the region of interest, ii) performing at least one fat saturation radio-frequency (RF) pulse or water excitation RF pulse to suppress signal from fat within the region of interest, iii) acquiring a first set of imaging data from the region of interest, and iv) repeating at least step i) and step iii) to acquire at least a second set of imaging data from the region of interest. The method further includes c) repeating step b) a predetermined number of times over a series of cardiac cycles to acquire respective sets of medical imaging data of the region of interest and d) reconstructing the first set of imaging data and the second set of imaging data into a time-resolved series of images.

In accordance with another aspect of the invention, a magnetic resonance imaging (MRI) system is disclosed that includes a magnet system configured to generate a polarizing magnetic field about at least a portion of a subject arranged in the MRI system, a plurality of gradient coils configured to apply a gradient field to the polarizing magnetic field, and a radio frequency (RF) system configured to apply an excitation field to the subject and acquire MR image data therefrom. A computer system is provided that is programmed to monitor a cardiac cycle of the subject to identify a predetermined point in the cardiac cycle. Upon identifying the predetermined point in the cardiac cycle, the computer is programmed to i) apply a magnetization suppressing preparation to suppress signal from blood flow through a region of interest and ii) apply at least one fat saturation radio-frequency (RF) pulse or water excitation RF pulse to suppress signal from fat within the region of interest. The computer is further programmed to iii) acquire a first set of imaging data from the region of interest and iv) repeat at least step i) and step iii) to acquire at least a second set of imaging data from the region of interest. The computer is further caused to repeat steps i) and iv) a predetermined number of times over a series of cardiac cycles to acquire respective sets of medical imaging data of the region of interest and reconstruct the first set of imaging data and the second set of imaging data into a time-resolved series of images.

In accordance with yet another aspect of the invention, a method for acquiring medical images of a portion of a vascular structure of a subject using a magnetic resonance imaging (MRI) system is disclosed. The method includes a) monitoring a cardiac cycle of the subject to identify a predetermined point in the cardiac cycle and, b) upon identifying the predetermined point in the cardiac cycle, performing the steps of i) performing at least one of the desired number of magnetization suppressing preparations to suppress signal from blood flow through at least the region of interest. The method also includes carrying out the steps of ii) acquiring a first set of imaging data from the region of interest and iii) repeating step i) and step ii) to acquire at least a second set of imaging data from the region of interest. The method further includes c) repeating step b) a predetermined number of times over a series of cardiac cycles to acquire respective sets of medical imaging data of the region of interest and d) reconstructing first set of imaging data and the second set of imaging data into a time-resolved series of images.

The foregoing and other advantages of the invention will appear from the following description. In the description, reference is made to the accompanying drawings which form a part hereof, and in which there is shown by way of illustration a preferred embodiment of the invention. Such embodiment does not necessarily represent the full scope of the invention, however, and reference is made therefore to the claims and herein for interpreting the scope of the invention.

DETAILED DESCRIPTION OF THE INVENTION

Figure 1:
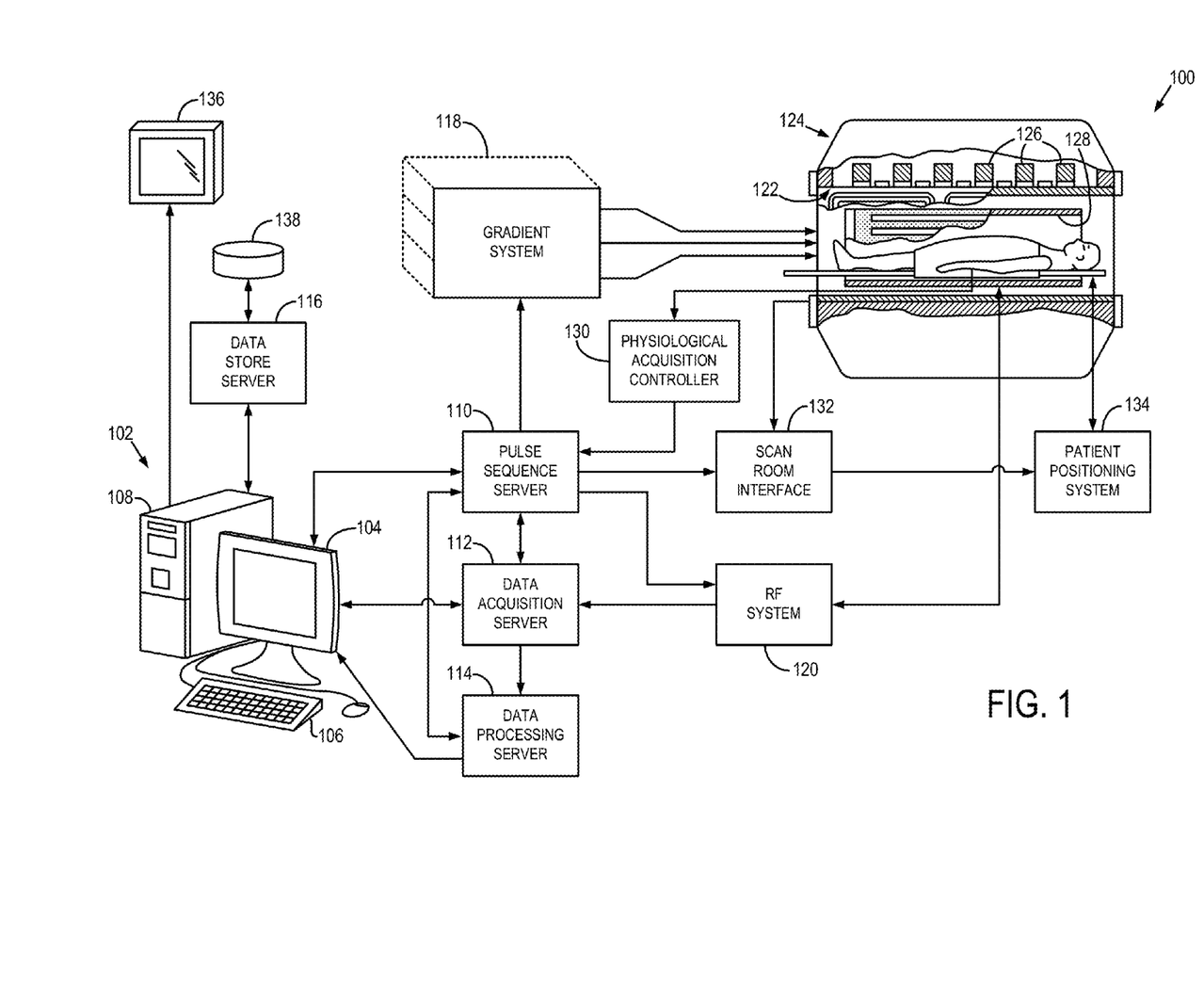
FIG. 1 is a block diagram of an MRI system for use with the present invention.

Referring particularly to FIG. 1, an example of a magnetic resonance imaging ("MRI") system 100 is illustrated. The workstation 102 includes a processor 108, such as a commercially available programmable machine running a commercially available operating system. The workstation 102 provides the operator interface that enables scan prescriptions to be entered into the MRI system 100. The workstation 102 is coupled to four servers: a pulse sequence server 110; a data acquisition server 112; a data processing server 114; and a data store server 116. The workstation 102 and each server 110, 112, 114, and 116 are connected to communicate with each other.

The pulse sequence server 110 functions in response to instructions downloaded from the workstation 102 to operate a gradient system 118 and a radiofrequency ("RF") system 120. Gradient waveforms necessary to perform the prescribed scan are produced and applied to the gradient system 118, which excites gradient coils in an assembly 122 to produce the magnetic field gradients Gx, Gy, and Gz used for position encoding MR signals. The gradient coil assembly 122 forms part of a magnet assembly 124 that includes a polarizing magnet 126 and a whole-body RF coil 128.

RF waveforms are applied to the RF coil 128, or a separate local coil (not shown in FIG. 2), by the RF system 120 to perform the prescribed magnetic resonance pulse sequence. Responsive MR signals detected by the RF coil 128, or a separate local coil (not shown in FIG. 1), are received by the RF system 120, amplified, demodulated, filtered, and digitized under direction of commands produced by the pulse sequence server 110. The RF system 120 includes an RF transmitter for producing a wide variety of RF pulses used in MR pulse sequences. The RF transmitter is responsive to the scan prescription and direction from the pulse sequence server 110 to produce RF pulses of the desired frequency, phase, and pulse amplitude waveform. The generated RF pulses may be applied to the whole body RF coil 128 or to one or more local coils or coil arrays (not shown in FIG. 1).

The RF system 120 also includes one or more RF receiver channels. Each RF receiver channel includes an RF preamplifier that amplifies the MR signal received by the coil 128 to which it is connected, and a detector that detects and digitizes the I and Q quadrature components of the received MR signal. The magnitude of the received MR signal may thus be determined at any sampled point by the square root of the sum of the squares of the and components:

$$M=\sqrt{I^2+Q^2} \quad \text{Eqn. (2);}$$

and the phase of the received MR signal may also be determined:

$$\varphi = \tan^{-1}\left(\frac{Q}{I}\right). \quad \text{Eqn. (3)}$$

The pulse sequence server 110 also optionally receives patient data from a physiological acquisition controller 130. The controller 130 receives signals from a number of different sensors connected to the patient, such as electrocardiograph ("ECG") signals from electrodes, or respiratory signals from a bellows or other respiratory monitoring device. Such signals are typically used by the pulse sequence server 110 to synchronize, or "gate," the performance of the scan with the subject's heart beat or respiration.

The pulse sequence server 110 also connects to a scan room interface circuit 132 that receives signals from various sensors associated with the condition of the patient and the magnet system. It is also through the scan room interface circuit 132 that a patient positioning system 134 receives commands to move the patient to desired positions during the scan.

The digitized MR signal samples produced by the RF system 120 are received by the data acquisition server 112. The data acquisition server 112 operates in response to instructions downloaded from the workstation 102 to receive the real-time MR data and provide buffer storage, such that no data is lost by data overrun. In some scans, the data acquisition server 112 does little more than pass the acquired MR data to the data processor server 114. However, in scans that require information derived from acquired MR data to control the further performance of the scan, the data acquisition server 112 is programmed to produce such information and convey it to the pulse sequence server 110. For example, during prescans, MR data is acquired and used to calibrate the pulse sequence performed by the pulse sequence server 110. Also, navigator signals may be acquired during a scan and used to adjust the operating parameters of the RF system 120 or the gradient system 118, or to control the view order in which k-space is sampled. By way of example, the data acquisition server 112 acquires MR data and processes it in real-time to produce information that may be used to control the scan.

The data processing server 114 receives MR data from the data acquisition server 112 and processes it in accordance with instructions downloaded from the workstation 102. Such processing may include, for example: Fourier transformation of raw k-space MR data to produce two or three-dimensional images; the application of filters to a reconstructed image; the performance of a backprojection image reconstruction of acquired MR data; the generation of functional MR images; and the calculation of motion or flow images.

Images reconstructed by the data processing server 114 are conveyed back to the workstation 102 where they are stored. Real-time images are stored in a data base memory cache (not shown in FIG. 1), from which they may be output to operator display 112 or a display 136 that is located near the magnet assembly 124 for use by attending physicians. Batch mode images or selected real time images are stored in a host database on disc storage 138. When such images have been reconstructed and transferred to storage, the data processing server 114 notifies the data store server 116 on the workstation 102. The workstation 102 may be used by an operator to archive the images, produce films, or send the images via a network to other facilities.

Figure 2:
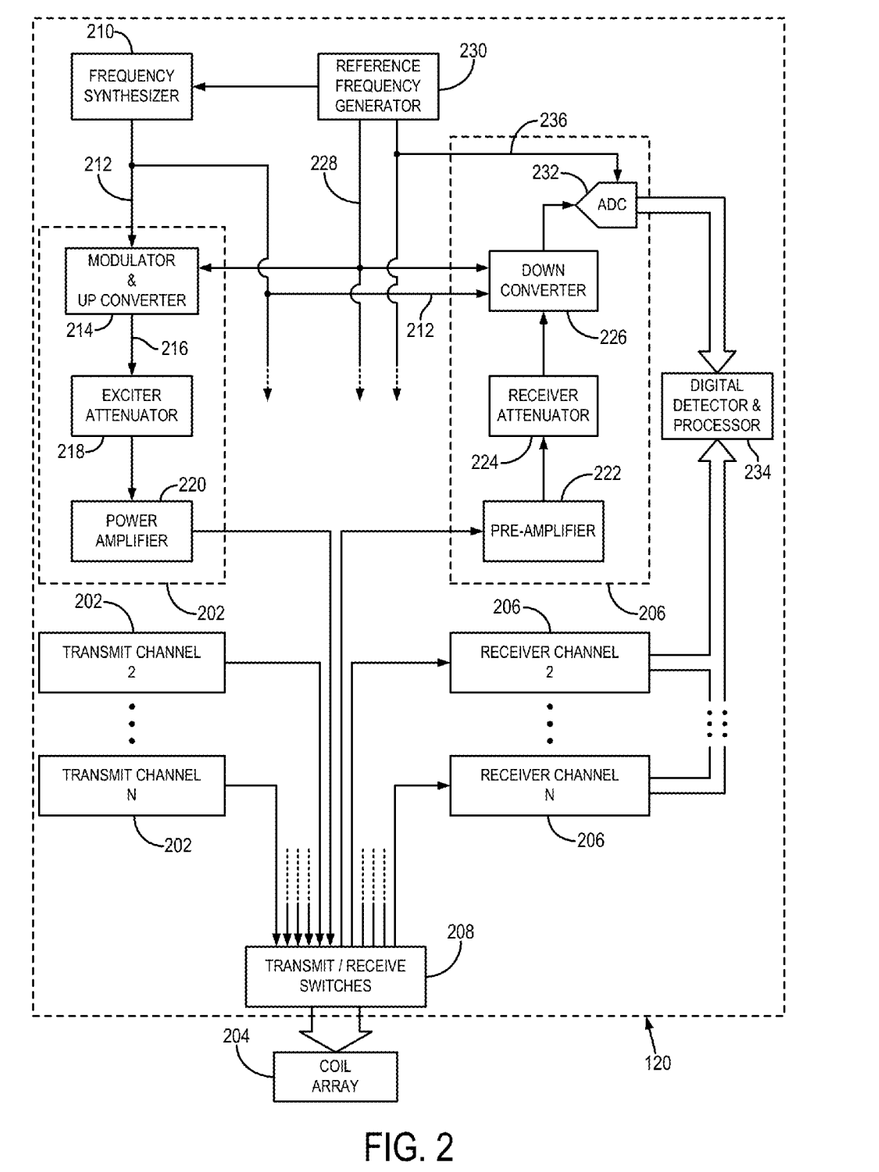
FIG. 2 is a schematic representation of a transceiver system for use with the MRI system of FIG. 1.

As shown in FIG. 1, the radiofrequency ("RF") system 120 may be connected to the whole body RF coil 128, or, as shown in FIG. 2, a transmission section of the RF system 120 may connect to one or more transmit channels 202 of an RF coil array 204 and a receiver section of the RF system 120 may connect to one or more receiver channels 206 of the RF coil array 204. The transmit channels 202 and the receiver channels 206 are connected to the RF coil array 204 by way of one or more transmit/receive ("T/R") switches 208.

Though illustrated as having multiple transmit channels 202 and multiple receiver channels 206 connected to multiple transmit/receive switches 208, the present invention is not limited to traditional or parallel imaging systems. However, as will be further made apparent below, the dual-contrast imaging technique to be described may particularly benefit from parallel imaging acceleration in the phase-encoding direction.

Also, the receiver channel 206 may also be an assembly of coils separate from the transmit coil array. In such a configuration, the T/R switches 208 are not needed. The transmit coil elements are detuned or otherwise rendered dysfunctional during the receive operation, and the receiver coil elements are similarly detuned or otherwise rendered dysfunctional during operation of the transmit coils. Such detuning may be accomplished with appropriate control logic signals.

Referring particularly to FIG. 2, the RF system 120 includes one or more transmit channels 202 that produce a prescribed RF electromagnetic field. The base, or carrier, frequency of this RF field is produced under control of a frequency synthesizer 210 that receives a set of digital signals from the pulse sequence server 110. These digital signals indicate the frequency, amplitude, and phase of the RF carrier signal produced at an output 212. The RF carrier is applied to a modulator and, if necessary, an up converter 214 where its amplitude and phase is modulated in response to a signal, R(t), also received from the pulse sequence server 110. The signal, R(t), defines the envelope of the RF pulse to be produced and is produced by sequentially reading out a series of stored digital values. These stored digital values may be changed to enable any desired RF pulse envelope to be produced.

The magnitude of the RF pulse produced at output 216 is attenuated by an attenuator circuit 218 that receives a digital command from the pulse sequence server 110. The phase of the RF pulse may also be altered using phase shifters (not shown). The modulated RF pulses are then applied to a power amplifier 220 that drives one element of the RF coil array 204, or several such elements that are electrically coupled. Multiple transmit channels then drive other elements of the multichannel transmit coil array.

The MR signal produced by the subject is picked up by the RF coil array 202 and applied to the inputs of the set of receiver channels 206. A preamplifier 222 in each receiver channel 206 amplifies the signal, which is then attenuated, if necessary, by a receiver attenuator 224 by an amount determined by a digital attenuation signal received from the pulse sequence server 110. The received signal is at or around the Larmor frequency, and this high frequency signal may be down converted in a two step process by a down converter 226. In an example of such a process, the down converter 226 first mixes the MR signal with the carrier signal on line 212 and then mixes the resulting difference signal with a reference signal on line 228 that is produced by a reference frequency generator 230. The MR signal is applied to the input of an analog-to-digital ("ND") converter 232 that samples and digitizes the analog signal. As an alternative to down conversion of the high frequency signal, the received analog signal can also be detected directly with an appropriately fast analog-to-digital ("A/D") converter and/or with appropriate undersampling. The sampled and digitized signal may then be applied to a digital detector and signal processor 234 that produces in-phase (I) and quadrature (Q) values corresponding to the received signal. The resulting stream of digitized I and Q values of the received signal are output to the data acquisition server 112. In addition to generating the reference signal on line 228, the reference frequency generator 230 also generates a sampling signal on line 236 that is applied to the A/D converter 232.

Figure 3:
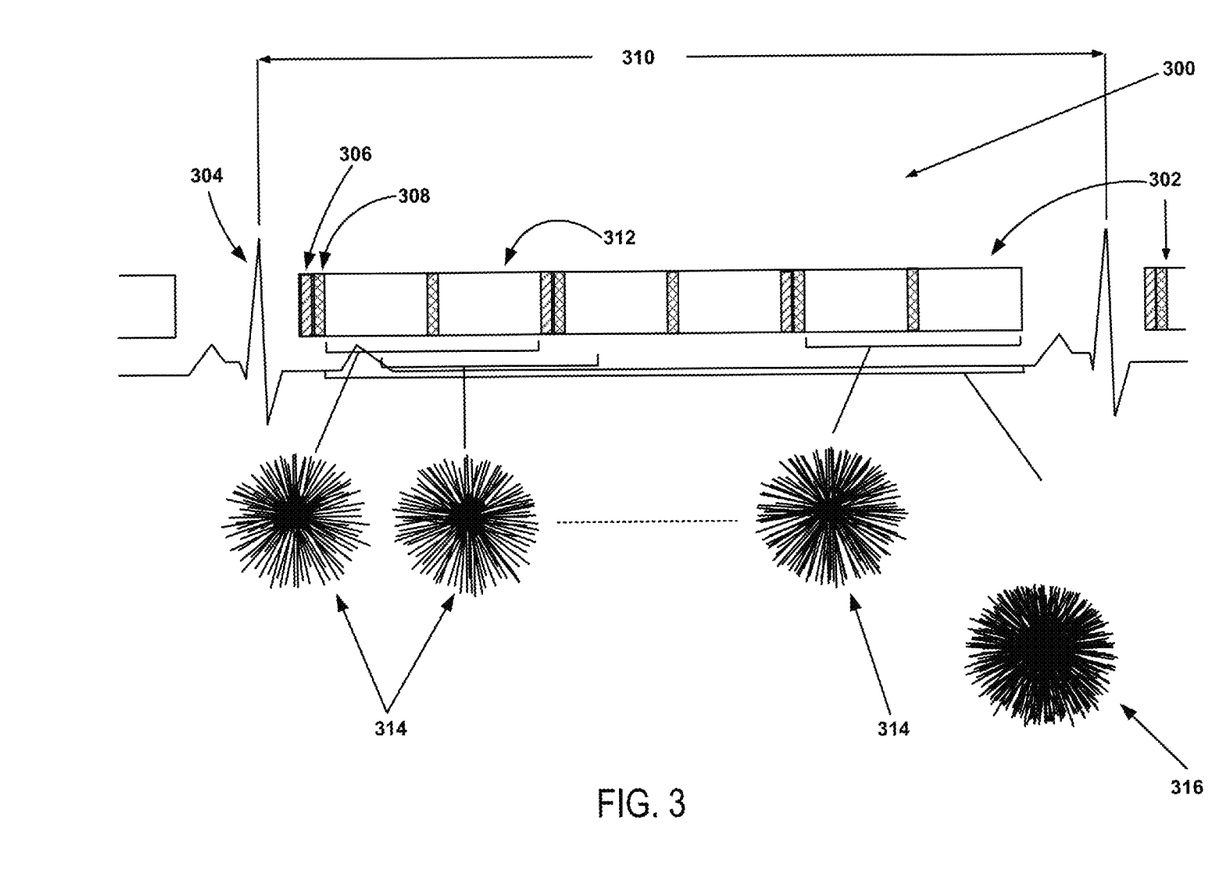
FIG. 3 is a schematic diagram of an imaging process in accordance with the present invention.

Referring to FIG. 3, the present invention provides 4D dark blood imaging technique 300 is schematically illustrated. As illustrated, the technique 300 includes a series of imaging data acquisitions, generally designated by arrow 302, that are gated, for example, using an electrocardiographic (ECG) waveform 304 or the like. That is, the imaging data acquisitions 302 may be iterated or divided based on the phases of the cardiac cycle, such as communicated by way of an ECG waveform 304. A given imaging data acquisition may include one or more motion sensitizing driven equilibrium (MSDE) preparations 306 and, optional, fat saturation RF pulses 308 that are interleaved into a general acquisition window 310 spanning a cardiac cycle. In the non-limiting example illustration, three MSDE preparations 306 and six fat saturation pulses 308 are applied. Arranged between these preparations/pulses are data acquisitions 312. The data acquisitions may be performed, for example, using a 3D gradient-echo pulse sequence or other pulse sequence suitable to yield uniform or quasi-uniform sampling at each reconstructed cardiac phase. In another embodiment, it should be noted that the fat saturation RF pulses 308 could be foregone and, for example, water selective excitation RF pulses used during data acquisitions 312 to elicit desirable contrast between the desired spin species.

Each data acquisition 312 yields a set of k-space data 314. As will be explained and as illustrated, the sets of k-space data 314, which are temporally resolved across the acquisition window and span the cardiac cycle, may be combined to form static or non-temporally resolved data set 316. In accordance with one implementation, which is illustrated in FIG. 3 but non-limiting, a 3D radial sampling may be used to create the k-space data 314 because it provides for large anatomical coverage with isotropic spatial resolution, supports the use of large undersampling factors, and is compatible with sliding window reconstruction. For example, it is contemplated that non-Cartesian sampling patters, such as 3D radial, cones, spiral, and the like, may be advantageously employed.

As noted above, ECG gating is used to enable time-resolved imaging over the cardiac cycle. Unlike prior 3D arterial wall imaging techniques that have applied MSDE preparations at, for example, a rate of approximately equal to the inverse of the spin-lattice relaxation time of blood (approximately 1 Hz) and have not used ECG gating, the presented invention applies multiple MSDE preparations in each heartbeat to achieve sustained suppression of flowing blood over the cardiac cycle. For example, MSDE preparations may be performed at a rate substantially greater than the inverse of the spin-lattice relaxation time of blood (approximately 2 Hz). Fat saturation RF pulses may be applied or water excitation RF pulses used throughout the echo train to suppress the signal intensity of perivascular fat.

Regardless of the specific parameters utilized, the present invention is designed to provide sustained and uniform suppression of the arterial blood pool to optimally depict, for example, the carotid arterial wall over the cardiac cycle. To determine preferable the number of MSDE preparations applied during each heartbeat (nMSDE), the number MSDE preparations applied in each heartbeat can be varied, for example, from 0 to 3. The static data set 316 can be used to reconstruct images and measure signals within the proximal internal carotid arterial wall and lumen (at the level of the carotid bulb). The signal-to-noise ratios of the arterial wall and the lumen, as well as the contrast-to-noise ratio between the wall and the lumen can be computed therefrom. Assuming that the noise is equal the standard deviation of air signal, the coefficient-of-variation of the signal within the internal carotid lumen in the cardiac phase-resolved series 314 can be considered to represent the consistency of blood suppression. The nMSDE configuration retaining near maximal contrast-to-noise ratio between the arterial wall and lumen on the static reconstruction and providing the best sustained suppression of the arterial lumen (smallest coefficient-of-variation) on the cardiac phase-resolved series can be considered optimal for many clinical applications.

Figure 4A:
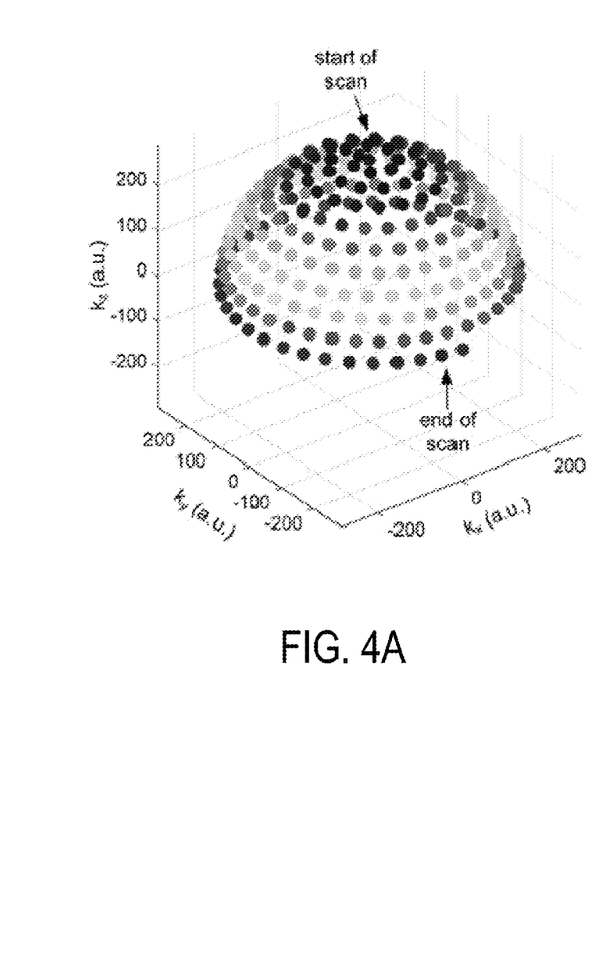
FIGS. 4A and 4B are exemplary plots of a k-space sampling trajectory that may, optionally, be used with the present invention.

In one exemplary implementation, radial projections may be sampled in a distribution and order previously described, with sampling commencing at a pole of the sampling sphere and spiraling down to the equator as the scan progressed, such as illustrated in FIG. 4A. Specifically, FIG. 4A is a point surface graph showing ends of acquired radial projections in 3D k-space. Sampling commences at a pole of the k-space sphere and spirals down to the equator (i.e., kz=0) over successive heartbeats.

Figure 4B:
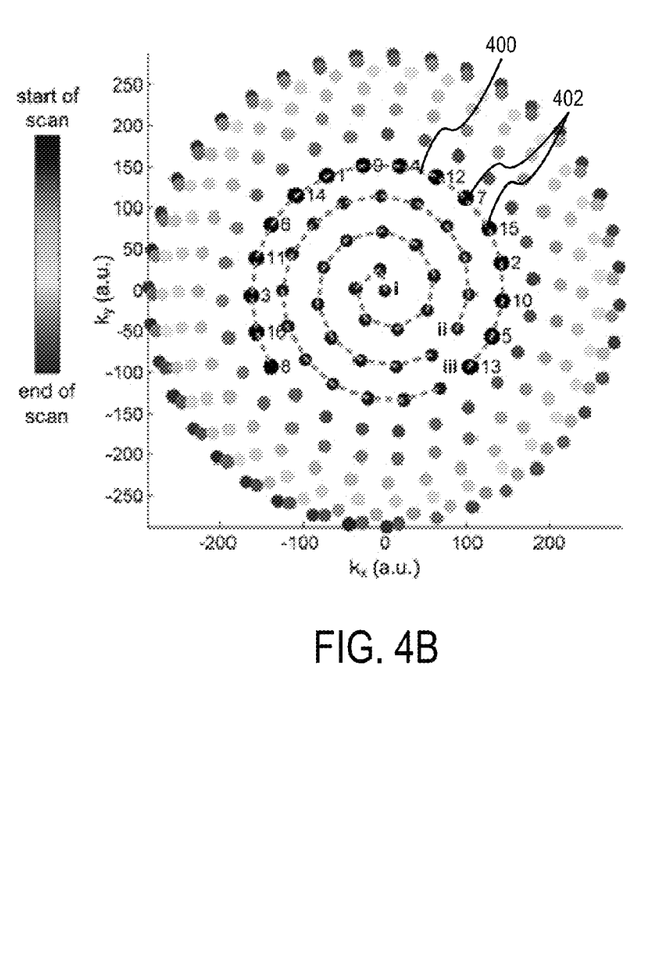

The number of heartbeats used for imaging may equate the total number of projections acquired in the scan divided by the number of projections acquired in each heartbeat (n). To facilitate reconstruction of an arbitrary number of cardiac phases of arbitrary temporal resolution with reduced artifacts, the n projections collected in each heart beat may be acquired in a quasi-golden ratio order, such as illustrated in FIG. 4B, according to the equation:

$$j = \lfloor \mod(i \times g, 1) \times n \rfloor + 1 \qquad \text{Eqn. (4);}$$

where j is the projection number, mod is the modulo operator, g is the golden mean $(|1-\sqrt{5}|)/2 \cong 0.618$), and i is incremented until all n lines are sampled once and only once. That is, FIG. 4B is k-space sampling of the kx-ky plane illustrating the pseudorandom golden ratio acquisition order used in each heartbeat. Projections acquired in the first three heartbeats are labeled (i-iii). Projections acquired in the same heartbeat are connected by dashed lines 400. The golden ratio acquisition order is defined for the 3rd heartbeat 402. Plots correspond to a trajectory of 256 projections with 16 projections acquired in each heartbeat. In practice, thousands of projections are acquired with tens to hundreds of projections acquired in each heartbeat.

Exemplary imaging parameters for the 4D dark blood arterial wall imaging sequence can be as follows: spoiled gradient-echo sequence with isotropic 0.8 mm spatial resolution; 288×288 matrix; isotropic 220 mm field-of-view; TR/TE/flip of 8.7 ms/4.2 ms/6°; 165 Hz/pixel receiver bandwidth; 30,008-30,150 projections per scan; 50-88 projections per heartbeat (heart rate dependent); 393-464 s acquisition time, 6-9 fat saturation RF pulses per heartbeat. Each MSDE preparation consisted of a $90_x$-$180_y$-$90_{-x}$ RF pulse sequence interposed with 4.0 ms long 15.0 mT/m gradients applied concurrently along three spatial axes of the scanner (first-order gradient moment of 982 mT·ms$^2$/m).

Following image data acquisition, unique images can be reconstructed. Specifically, if the data was acquired as radially sampled data, reconstruction may begin with gridding onto a rectilinear k-space grid using, for example, a Kaiser Bessel kernel of width 3 and β=4.2054. Data from multiple receiver elements can be combined using standard methods such as sum of squares or adaptive coil combination. Alternatively, gridding may be foregone in favor of a projection-reconstruction algorithm.

As described above, a series of cardiac phase-resolved image sets and one static reconstruction can be generated. That is, in addition to the series of cardiac phase-resolved reconstructions, a static high resolution 3D dark-blood angiogram was obtained by gridding all acquired projections with use of a uniform k-space weighting function.

For cardiac phase-resolved imaging, a series of temporal phases (for example, $\varphi_1$ through $\varphi_{20}$) may be reconstructed by gridding projections within a limited temporal window width ($\tau_W$) at 20 temporal positions ($\tau_1$ through $\tau_{20}$) in the cardiac cycle. In generating temporal phase $\varphi_c$ (centered at time point $\tau_c$), a sample located at a position $k_x$ on projection p may be weighted prior to gridding according to the equation:

$$w(\Delta\tau, \Delta k_x) = f(\Delta\tau) + \Delta k_x^2 [1 - f(\Delta\tau)]\left(\frac{2}{n_x}\right)^2; \quad \text{Eqn. (5)}$$

where $$f(\Delta\tau) = (\tau_w - \Delta\tau)^2 \left(\frac{2}{\tau_w}\right)2,$$

Figure 5:
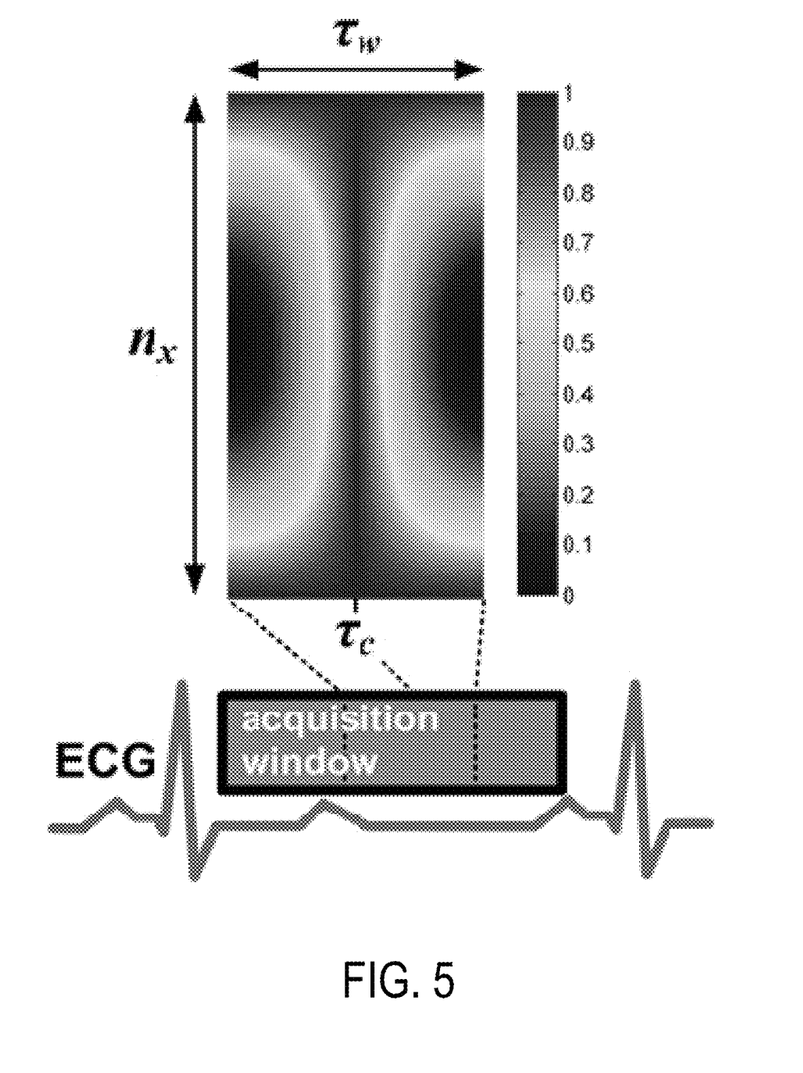
FIG. 5 is a plot of a k-space weighting function in accordance with the present invention.

$n_x$ is the number of readout points in the projection, $\Delta\tau$ is temporal displacement of the projection of interest, computed as $\Delta\tau = |\tau_p - \tau_c|$ where $\tau_p \in [\tau_c - \tau_w/2, \tau_c + \tau_w/2]$ is the temporal position of the projection, and $\Delta k_x$ is the displacement of the sample from central k-space ($n_x/2$), computed as $\Delta k_x = |k_x - n_x/2|$ where $k_x \in [1, n_x]$. Weights for projections outside of the temporal window may be set to zero. This weighting scheme is illustrated in FIG. 5 and restricts the temporal window at the center of k-space to faithfully capture rapid changes in image contrast while gridding a substantial number of points at the periphery of k-space to maintain sufficient spatial resolution. Specifically, as illustrated in FIG. 5, weights outside of the temporal width of the reconstruction window, $\tau_w$, equal zero. In this illustration, $\tau_w$ comprises 40% of the acquisition window width (i.e., $\tau_w$=0.4). The weighting function may be circularly wrapped to reconstruct early and late temporal phases located at the ends of the data acquisition window. Other weighting functions may be used including, but not limited to, tornado (Barger, A. V., Block, W. F., Toropov, Y., Grist, T. M. and Mistretta, C. A., Time-resolved contrast-enhanced imaging with isotropic resolution and broad coverage using an undersampled 3D projection trajectory. Magnetic Resonance Medicine, 2002; 48: 297-305) and KWIC (Song, H. K. and Dougherty, L., k-Space weighted image contrast (KWIC) for contrast manipulation in projection reconstruction MRI. Magnetic Resonance Medicine, 2000; 44: 825-832).

Advantageously, the present invention can be compared to prior-art methods for performing MRA. As described above, an optimal or advantageous number of MSDE preparations can be determined for a particular clinical application. For example, one process considered 8 healthy subjects (5 females, age 45.9±12.1 years, weight 74.3±8.3) and one a 78-year-old male patient with sonographically documented internal carotid arterial stenosis. In the eight healthy subjects, validation of arterial kinematics as depicted on the cardiac phase-resolved 4D dark-blood reconstructions was made by comparing arterial luminal areas with respect to multi-slice 2D cineangiographic (cine) FLASH imaging. 2D cine FLASH imaging was performed using the same acquisition window duration of the 4D dark blood sequence with the following additional parameters: 14 axial slices; 0.8 mm in plane resolution; 3 mm slice resolution; 200×200 matrix; 20 reconstructed temporal phases per cardiac cycle (34-50 ms per phase); TR/TE/flip of 8.4-11.2 ms/4.4-5.9 ms/12°; 250-425 Hz/pixel receiver bandwidth. The temporal reconstruction window width parameter, $\tau_w$, of the 4D dark blood method was varied from 10% to 40% of the cardiac cycle (in 10% increments) to assess its impact on measured arterial luminal area; $\tau_w$ values less than 10% were not considered because they provided poor display of the arterial wall.

Validation of the reconstructed static high resolution dark-blood angiograms was made by comparing arterial wall areas with respect to a non-cardiac-gated 3D dark-blood MERGE acquisition (Balu, N., Yarnykh, V. L., Chu, B., Wang, J., Hatsukami, T. and Yuan, C., Carotid plaque assessment using fast 3D isotropic resolution black-blood MRI. Magnetic Resonance Medicine, 2011:65: 627-637). Imaging parameters of the correlative 3D MERGE sequence were: coronal slab orientation; isotropic 0.8 mm resolution; 288×200 matrix; 96 slices; TR/TE/flip of 8.7 ms/3.5 ms/6°; 165 Hz/pixel receiver bandwidth; 100 lines per segment; application of 1 MSDE preparation with a first-order gradient moment of 1453 mT·ms$^2$/m every 911 ms; 3 signal averages; 263 s acquisition time. MERGE imaging was not performed in one subject due to premature study termination.

Quantitative analyses were performed in one randomly selected carotid artery per subject. To facilitate comparison of arterial motion with respect to the 14 2D cine FLASH slices acquired in each subject, cardiac phase-resolved 4D dark blood imaging data were reformatted into 14 3-mm-thick transversal slices. Measures of arterial lumen and wall areas for all acquisitions (2D cine FLASH, cardiac phase-resolved 4D, static 3D MERGE, and static 4D) were made using an objective semi-automated segmentation and measurement method. Measurements obtained at locations where arterial boundaries were erroneously segmented, due either to low signal or gross motion artifact, were eliminated from further analysis. Correspondence and agreement of arterial areas was assessed through linear regression and Bland-Altman analyses. Probability values less than 0.05 were considered to indicate statistical significance. Statistical analyses were performed in commercial software (SPSS Statistics 17.0, SPSS Inc., Chicago, Ill.).

Following below are the results for various clinical applications.

Blood Suppression Optimization Study

Figure 6A:
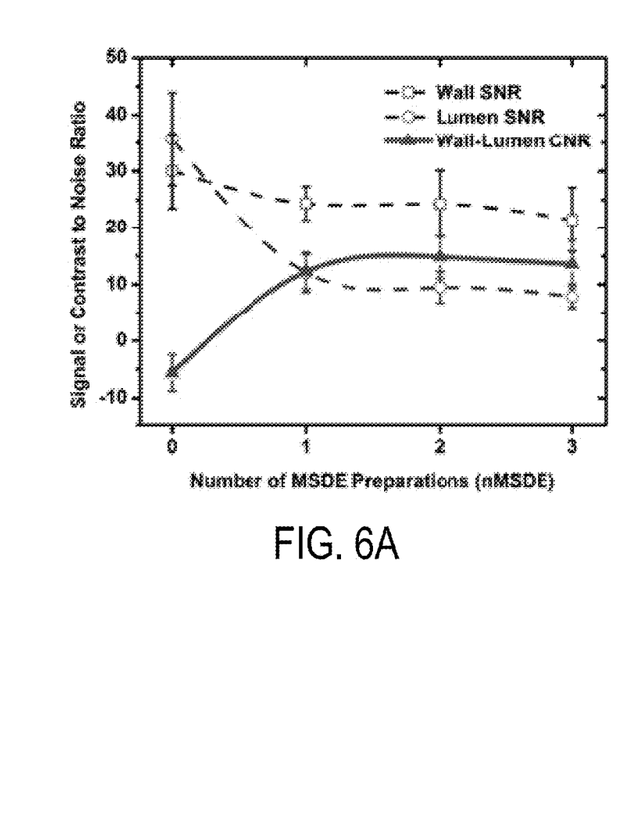
FIGS. 6A and 6B are plots of data collected during a blood suppression optimization study in accordance with the present invention.
Figure 6B:
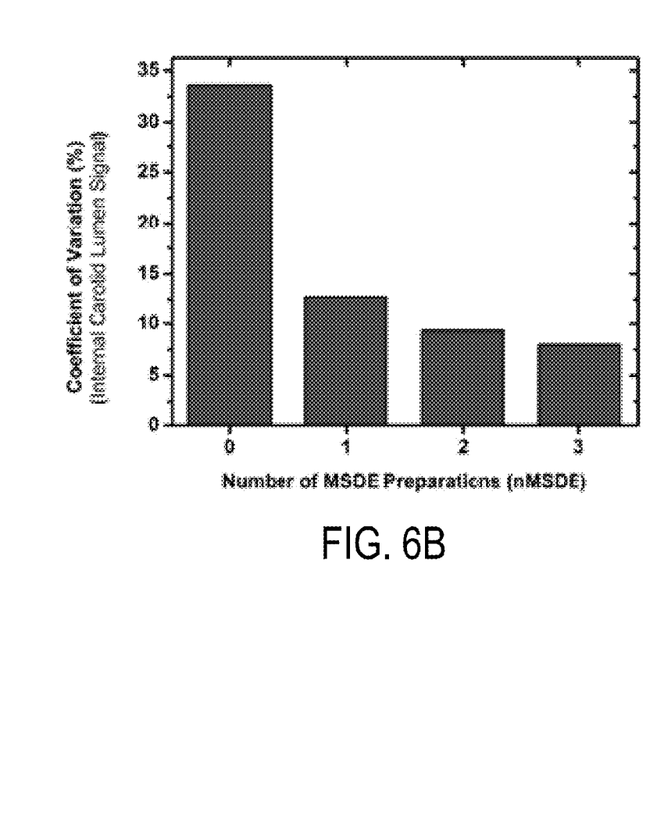

The results of the flow optimization study are summarized in FIGS. 6A and 6B. The application of three MSDE preparations in each heart beat are illustrated in FIGS. 6A and 6B, where FIG. 6A shows the wall-lumen contrast-to-noise ratio of the static reconstruction was maintained and FIG. 6B shows the smallest coefficient of signal variation within internal carotid lumen in the time resolved reconstructions was provided. In FIG. 6B, data was obtained with $\tau_w$ spanning 40% of the total acquisition window width. The uniformity of blood signal suppression improved as the number of MSDE pulses (nMSDE) applied in each heartbeat increased. Execution of 3 MSDE preparations within each heartbeat minimized the signal-to-noise ratio of the carotid blood pool, provided near optimal wall-lumen contrast-to-noise ratio, and minimized the coefficient-of-variation of signal within the arterial lumen.

4D Dark Blood Arterial Wall MR Imaging Results

Time resolved and static, high-resolution images of the carotid bifurcation were obtained with the present invention. The images displayed the pulsating motions of the healthy and diseased carotid arterial walls with dark blood contrast throughout the cardiac cycle. Consistent with the intermittent application of the MSDE preparations, the degree of arterial blood suppression transiently improved when the MSDE preparations were applied. The use of 3 MSDE pulses within each cardiac cycle suppressed slow-moving, recirculating flow in the internal carotid arterial bulb. Fat was well suppressed throughout the cardiac cycle, which enabled delineation of the outer boundaries of the vessels.

Measurements of Arterial Lumen Area

Out of a total of 112 slice locations of acquired data, 7 locations (6.25%) were eliminated from analysis due either to low signal at 4D MRI (n=4) or artifact on the 2D cine FLASH images (n=3). Table 1 summarizes the linear regression and Bland-Altman analyses of the remaining slices and temporal frames (n=105×20=2100).

tion temporal window parameter, $\tau_w$, was shortened. The span of the 95 percent limits of agreement increased as $\tau_w$ was decreased, reflecting greater variability.

Figure 7:
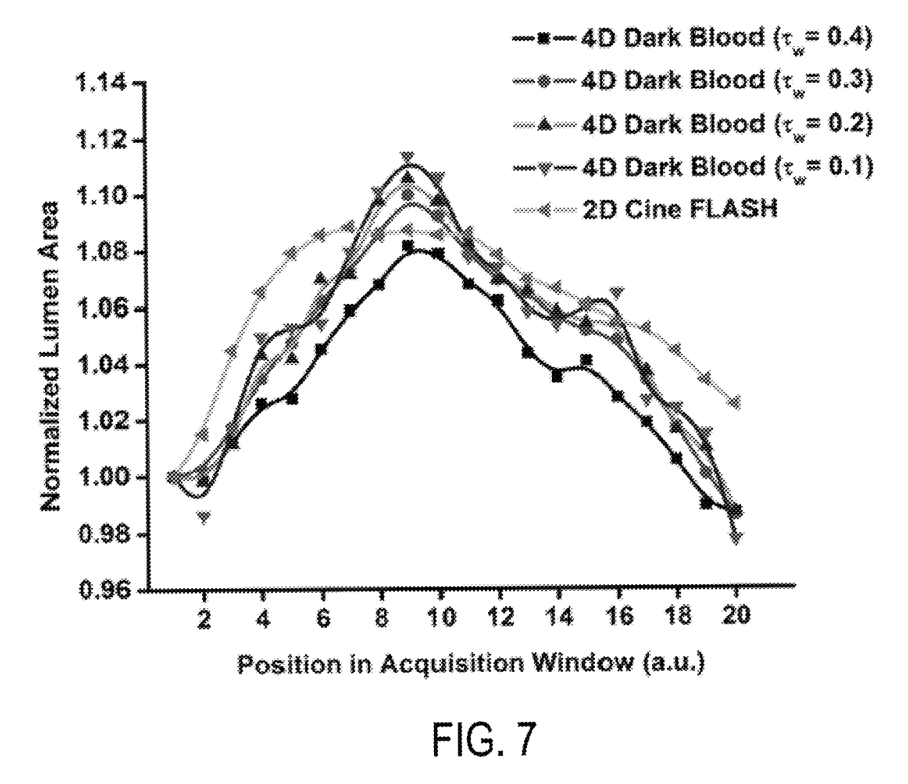
FIG. 7 is a plot of arterial lumen area versus temporal position in the acquisition window as obtained with 2D cine fast low angle shot (FLASH) imaging technique and the 4D dark blood imaging technique of the present invention.

FIG. 7 is a graph showing the change in arterial lumen area over the acquisition window, which spanned the majority of the cardiac cycle. Compared to the first reconstructed frame, carotid lumen area increased to a maximum value near the midpoint of the acquisition window; this increase was inversely associated with $\tau_w$. Very good correlation between all 4D dark blood MRI reconstructions and 2D cine FLASH data was found, with r values ranging from 0.884 to 0.915 ($P<1\times10^{-6}$).

Measurements of Arterial Wall Area

Figure 8A:
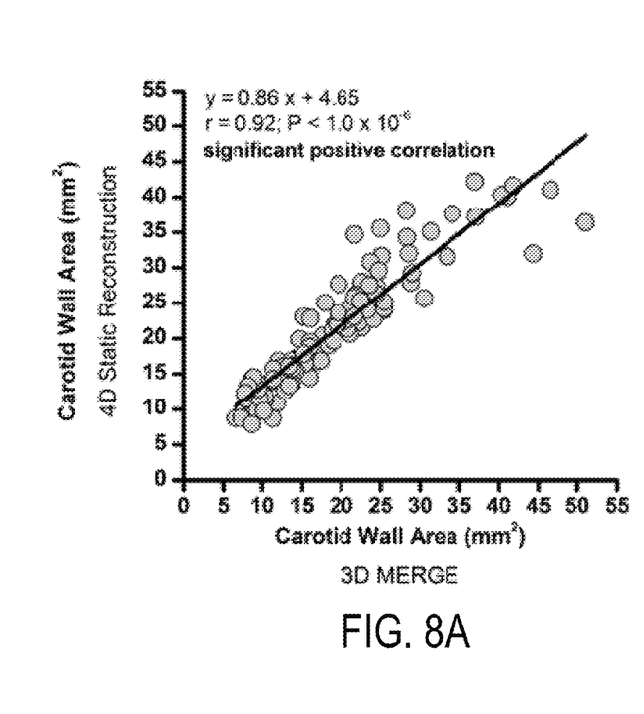
FIGS. 8A and 8B are graphs comparing the arterial wall areas derived from the static reconstruction of the 4D dark blood MRI imaging technique in accordance with the present invention and the established 3D dark blood MERGE method.
Figure 8B:
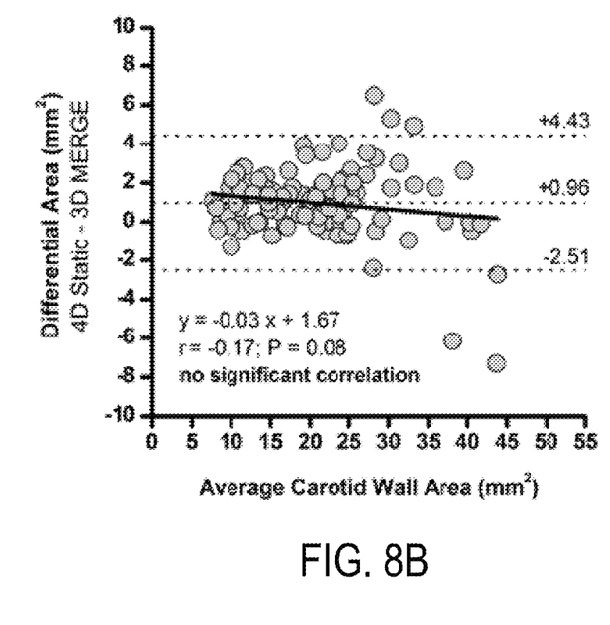

Arterial wall areas derived from the static reconstruction of the 4D dark blood MRI imaging technique in accordance with the present invention and the established 3D dark blood MERGE method are shown in FIGS. 8A and 8B. Good correlation between measurements was observed (r=0.920; $P<1\times10^{-6}$) and Bland-Altman analysis revealed a mean arterial wall area difference of 0.96 mm². No data were eliminated due to poor image quality or erroneous vessel segmentation. Excellent correspondence in spatial resolution and arterial wall depiction was observed.

The present invention provides a 4D MRI method tailored for visualizing the arterial wall with dark-blood contrast and fine isotropic spatial resolution. The methods of the present invention have been shown to depict the temporal dynamics of the carotid arteries with good agreement to bright-blood cineangiographic data, and provided a high spatial resolution static dark-blood MR angiogram that was comparable in quality to that provided by an established state-of-the-art 3D dark blood imaging protocol.

Prior ultrasound (US) studies have raised the notion and brought forth evidence that carotid plaque motion may be predictive of risk for future cerebrovascular events. Being a real-time and inexpensive modality, US may be particularly well suited for investigation of carotid wall kinematics. US, however, depicts vascular motion on a 2D plane and is limited by acoustic shadowing in the presence of calcification, a common finding in atherosclerosis of the carotid arteries and other vascular beds. Three-dimensional and 4D US may provide more comprehensive data but these meth-

TABLE 1

Carotid Lumen Area: 4D Dark Blood MRI Versus 2D Cine FLASH

| Comparison[c] | Linear Regression[a] | | | Bland-Altman[b] | | |
|---|---|---|---|---|---|---|
| | Best Fit Line | r | P-value | Mean Difference (%) | 95% Limits of Agreement (%) | Span of Limits of Agreement (%) |
| $T_w = 0.4$ | 0.941x + 6.636 | 0.898 | $<1 \times 10^{-6}$ | −4.5 | (−23, +14) | 37 |
| $T_w = 0.3$ | 0.940x + 6.279 | 0.899 | $<1 \times 10^{-6}$ | −4.0 | (−23, +15) | 38 |
| $T_w = 0.2$ | 0.942x + 5.707 | 0.896 | $<1 \times 10^{-6}$ | −3.2 | (−23, +16) | 39 |
| $T_w = 0.1$ | 0.928x + 4.933 | 0.892 | $<1 \times 10^{-6}$ | −1.5 | (−22, +19) | 41 |

[a] 4D dark blood MRI vs. 2D cine FLASH.
[b] 4D dark blood MRI minus 2D cine FLASH; values given as a percentage of the mean obtained with both methods.
[c] $T_w$ values given as fractions of the acquisition window duration.
Data derived from 2100 measurements.

Very good correlation between 4D dark blood MRI and 2D cine FLASH measurements was found (r values ranging from 0.892 to 0.899; P values$<1\times10^{-6}$). Compared to the mean values of both methods, 4D dark blood MRI slightly underestimated arterial luminal area by 1.5 percent to 4.5 percent. This underestimation decreased as the reconstrucods are still limited by calcification, and require specialized hardware and non-trivial data processing which limit widespread use. Furthermore, use of these advanced US methods in other vascular territories requires an acoustic window.

Unlike US, the MR methodology of the present invention is not affected by calcification or dependent on the presence of an acoustic window. In evaluating of atherosclerosis, the methods of the present invention complement existing static MR plaque imaging sequences (such as 2D fast spin echo and 3D dark blood MERGE) by providing information about arterial wall and plaque kinematics. As implemented, 4D method of the present invention is rapid, as it can be performed in, for example, 6-8 minutes of scan time or less. On the basis of the satisfactory results obtained at shorter temporal reconstruction window widths (e.g., $\tau_w=0.2$ and 0.3, Table 1), it is feasible to shorten scan time to approximately 5 minutes or less by acquiring fewer projections. Quantitative measures of arterial wall area also show that the static 3D dark blood angiogram derived from the 4D protocol can eliminate the need for acquiring a standalone 3D dark blood FLASH sequence. Although the presented 4D dark blood technique was applied to the carotid arteries and described with respect to a 3 T MRI system, it is noted that the technique can be readily used on other magnetic field strengths and to image other vascular beds. Data acquired in laboratory tests have shown that the method can be applied at 1.5 T and can image other vessels including the aorta, iliac, femoral, popliteal arteries, and the like.

A golden ratio projection ordering scheme, such as described above can be used to support arbitrary temporal resolutions while controlling artifacts in the cardiac phase-resolved reconstructions. Other projection ordering schemes that provide uniform or quasi-uniform sampling of k-space for the time-resolved series may be used. It should be noted, however, that projection ordering schemes that do not provide uniform or quasi-uniform k-space sampling can be used but may produce substantial artifacts in the time-resolved series that may obscure display of the arterial wall. It is also contemplated that other (i.e. non-radial) 3D sampling trajectories be used with the present invention, so long as these trajectories routinely sample the center of k-space. A drawback of the k-space trajectory used here is the process of gridding reconstruction which is computationally intensive. Thus, other sampling techniques or projection reconstruction techniques may be used.

Therefore, the present invention uses multiple MSDE preparations applied in each heartbeat to suppress the appearance of the blood pool throughout the cardiac cycle. To limit reduction of signal from static non-vascular tissue as a consequence of applying these MSDE preparations, each MSDE preparation may apply only a moderate first-order gradient moment of $\approx 1000$ mT·ms$^2$/m. It is acknowledged that the number of MSDE preparations can be selected to achieve a requisite degree of blood signal suppression and will depend on the configuration of the MSDE preparations and its first-order gradient moment, as well as the blood flow characteristics of the target vasculature, and should be tuned accordingly.

Thus, the present invention provides a 4D dark blood MR method that can depict the pulsatile motion of the human arterial wall in three spatial dimensions over the cardiac cycle. The method provides for submillimeter isotropic definition of the carotid arterial wall and its motion, and can also provide a static high spatial resolution dark blood angiogram of the carotid bifurcation. With respect to depicting carotid arterial pulsation, the method is in good agreement with 2D cine FLASH imaging, and results were consistent with published US measures of carotid distension over the cardiac cycle.

The present invention has been described in terms of one or more preferred embodiments, and it should be appreciated that many equivalents, alternatives, variations, and modifications, aside from those expressly stated, are possible and within the scope of the invention.

The invention claimed is:

1. A method for acquiring medical images of a portion of a vascular structure of a subject using a magnetic resonance imaging (MM) system, the method comprising the steps of:
   a) determining a desired number of motion sensitizing driven equilibrium (MSDE) preparations to be applied to the subject within one cardiac cycle of the subject to sustain a suppression of signal from blood flow through at least a region of interest, wherein the desired number can be varied;
   b) monitoring a cardiac cycle of the subject to identify a predetermined point in the cardiac cycle and, upon identifying the predetermined point in the cardiac cycle, performing the steps of:
      i) performing at least one of the desired number of the MSDE preparations to suppress signal from blood flow through at least the region of interest;
      ii) performing at least one of a fat saturation radio-frequency (RF) pulse and water excitation RF pulse to control signal from fat within the region of interest relative to signal from non-fat;
      iii) acquiring a first set of imaging data from the region of interest;
      iv) repeating at least step i) and step iii) to acquire at least a second set of imaging data from the region of interest;
   c) repeating step b) a predetermined number of times over a series of cardiac cycles to acquire respective sets of medical imaging data of the region of interest; and
   d) reconstructing the first set of imaging data and the second set of imaging data into a time-resolved series of images.

2. The method of claim 1 further comprising combining at least portions of the first set of imaging data and the second set of imaging data and reconstructing a static image from the common cardiac cycle.

3. The method of claim 1 further comprising combining at least portions of a plurality of sets of time-resolved series of images spanning multiple cardiac cycles and reconstructing a composite static image spanning multiple cardiac cycles.

4. The method of claim 1 wherein step d) includes combining portions of the respective sets of medical imaging data and reconstructing the time-resolved series of images across multiple cardiac cycles.

5. The method of claim 1 wherein the desired number of magnetization suppressing preparations in step a) is selected to suppress signal from blood over the cardiac cycle in spite of spin-lattice relaxation.

6. The method of claim 1, wherein the desired number of the MSDE preparations in step a) is selected based on configuration of the MSDE preparations and a first-order gradient moment of each MSDE preparation.

7. The method of claim 1 wherein step b)iii) includes acquiring k-space data from the subject in a manner that yields at least one of uniform and quasi-uniform sampling pattern.

8. The method of claim 1 wherein step b)iii) includes acquiring k-space data using a non-Cartesian sampling pattern.

9. The method of claim 1 wherein step b) includes identifying an acquisition window within the cardiac cycle and performing steps b)i) through b)iii) within the acquisition window.

10. The method of claim 1 wherein the step b)i) is repeated at a rate greater than an inverse of the spin lattice relaxation time of blood.

11. A magnetic resonance imaging (MRI) system comprising:
a magnet system configured to generate a polarizing magnetic field about at least a portion of a subject arranged in the MM system;
a plurality of gradient coils configured to apply a gradient field to the polarizing magnetic field;
a radio frequency (RF) system configured to apply an excitation field to the subject and acquire MR image data therefrom;
a computer system programmed to:
monitor a cardiac cycle of the subject to identify a predetermined point in the cardiac cycle and, upon identifying the predetermined point in the cardiac cycle, performing the steps of:
i) determine a desired number of motion sensitizing driven equilibrium (MSDE) preparations to be applied to the subject within the cardiac cycle of the subject, and apply the desired number of the MSDE preparations to suppress signal from blood flow through a region of interest, wherein the desired number can be varied;
ii) apply at least one of a fat saturation radio-frequency (RF) pulse and water excitation RF pulse to control signal from fat within the region of interest relative to signal from non-fat within the region of interest;
iii) acquire a first set of imaging data from the region of interest;
iv) repeat at least step i) and step iii) to acquire at least a second set of imaging data from the region of interest;
repeat steps i) and iv) a predetermined number of times over a series of cardiac cycles to acquire respective sets of medical imaging data of the region of interest; and
reconstruct the first set of imaging data and the second set of imaging data into a time-resolved series of images.

12. The MM system of claim 1 wherein reconstructing includes combining portions of the respective sets of medical imaging data and reconstructing the time-resolved series of images from portions of the first set of imaging data and the second set of imaging data within common portions of multiple cardiac cycles.

13. The MM system of claim 11 further comprising combining at least portions of the first set of imaging data and the second set of imaging data and reconstructing a static image from the common cardiac cycle.

14. The MRI system of claim 11 further comprising combining at least portions of a plurality of sets of time-resolved series of images spanning multiple cardiac cycles and reconstructing a composite static image spanning multiple cardiac cycles.

15. A method for acquiring medical images of a portion of a vascular structure of a subject using a magnetic resonance imaging (MM) system, the method comprising the steps of:
a) monitoring a cardiac cycle of the subject to identify a predetermined point in the cardiac cycle;
b) upon identifying the predetermined point in the cardiac cycle, performing the steps of:
i) determining a desired number of motion sensitizing driven equilibrium (MSDE) preparations to be applied to the subject within the cardiac cycle of the subject, and performing the desired number of the MSDE preparations to suppress signal from blood flow through at least a region of interest, wherein the desired number can be varied;
ii) acquiring a first set of imaging data from the region of interest;
iii) repeating step i) and step ii) to acquire at least a second set of imaging data from the region of interest;
c) repeating step b) a predetermined number of times over a series of cardiac cycles to acquire respective sets of medical imaging data of the region of interest; and
d) reconstructing the first set of imaging data and the second set of imaging data into a time-resolved series of images.

16. The method of claim 15 further comprising determining the desired number of the MSDE preparations to be applied to the subject within one cardiac cycle of the subject based on configuration of the MSDE preparations and a first-order gradient moment of each magnetization suppressing preparation.

17. The MM system of claim 15 wherein reconstructing includes combining portions of the respective sets of medical imaging data and reconstructing the time-resolved series of images from portions of the first set of imaging data and the second set of imaging data within common portions of multiple cardiac cycles.

18. The method of claim 15 further comprising at least one of:
combining at least portions of the first set of imaging data and the second set of imaging data and reconstructing a static image from the common cardiac cycle; and
combining at least portions of a plurality of sets of time-resolved series of images spanning multiple cardiac cycles and reconstructing a composite static image spanning multiple cardiac cycles.

* * * * *

UNITED STATES PATENT AND TRADEMARK OFFICE
CERTIFICATE OF CORRECTION

PATENT NO. : 9,968,276 B2  
APPLICATION NO. : 13/647119  
DATED : May 15, 2018  
INVENTOR(S) : Ioannis Koktzoglou Page 1 of 1

It is certified that error appears in the above-identified patent and that said Letters Patent is hereby corrected as shown below:

Column 7, Line 18, "("ND")" should be --("A/D")--.

Column 8, Line 15, "approximately 2" should be --approximately $\geq 2$--.

Column 14, Claim 1, Line 7, "(MM)" should be --(MRI)--.

Column 15, Claim 11, Line 8, "(MM)" should be --(MRI)--.

Column 15, Claim 12, Line 43, "(MM)" should be --(MRI)--.

Column 15, Claim 13, Line 49, "(MM)" should be --(MRI)--.

Column 16, Claim 15, Line 8, "(MM)" should be --(MRI)--.

Column 16, Claim 17, Line 37, "(MM)" should be --(MRI)--.

Signed and Sealed this  
Tenth Day of July, 2018

Andrei Iancu  
*Director of the United States Patent and Trademark Office*